US012685603B2

(12) United States Patent     (10) Patent No.:   US 12,685,603 B2

Ramadorai     (45) Date of Patent:   *Jul. 21, 2026

(54) SYSTEMS, METHODS, AND COMPUTER-READABLE PROGRAM PRODUCTS FOR CONTROLLING A ROBOTICALLY DELIVERED MANIPULATOR

(71) Applicant: Covidien LP, Mansfield, MA (US)

(72) Inventor: Arvind Ramadorai, Lexington, MA (US)

(73) Assignee: Covidien LP, Mansfield, MA (US)

( * ) Notice: Subject to any disclaimer, the term of this patent is extended or adjusted under 35 U.S.C. 154(b) by 57 days.

This patent is subject to a terminal disclaimer.

(21) Appl. No.: 18/116,959

(22) Filed: Mar. 3, 2023

(65) Prior Publication Data

US 2023/0200923 A1     Jun. 29, 2023

Related U.S. Application Data

(63) Continuation of application No. 16/306,605, filed as application No. PCT/US2017/035576 on Jun. 2, 2017, now Pat. No. 11,612,446.

(Continued)

(51) Int. Cl.
    *A61B 34/30*       (2016.01)
    *A61B 34/00*       (2016.01)
    (Continued)

(52) U.S. Cl.
    CPC .............. *A61B 34/37* (2016.02); *A61B 34/25* (2016.02); *A61B 34/30* (2016.02); *G06F 3/011* (2013.01);
             (Continued)

(58) Field of Classification Search
    CPC ...................... A61B 34/30; A61B 2017/00207
    See application file for complete search history.

(56) References Cited

U.S. PATENT DOCUMENTS 6,132,368 A    10/2000   Cooper
6,206,903 B1    3/2001   Ramans
                (Continued)

FOREIGN PATENT DOCUMENTS

CN       102018572 A     4/2011
CN       102647955 A     8/2012
                (Continued)

OTHER PUBLICATIONS

Extended European Search Report dated May 28, 2020 corresponding to counterpart Patent Application EP 17807527.1.

(Continued)

*Primary Examiner* — Henry Orr
(74) *Attorney, Agent, or Firm* — Carter, DeLuca & Farrell, LLP

(57) ABSTRACT

Systems, methods, and computer-readable media are provided for controlling a robotically delivered manipulator. One system includes a robotic manipulator having a base and a surgical instrument holder configured to move relative to the base, a surgical instrument removably coupled to the surgical instrument holder, a user interface configured to present information related to least one of the robotic manipulator or the surgical instrument, a gesture detection sensor configured to detect a gesture made by a user representing a desired movement of the robotic manipulator, and a controller configured to actuate the robotic manipulator in a predetermined manner corresponding to the detected gesture.

8 Claims, 8 Drawing Sheets

Related U.S. Application Data

(60) Provisional application No. 62/345,054, filed on Jun. 3, 2016.

(51) Int. Cl.

| | |
|---|---|
| *A61B 34/37* | (2016.01) |
| *G06F 3/01* | (2006.01) |
| *G06F 3/033* | (2013.01) |
| *G06F 3/0488* | (2022.01) |
| *G06F 3/04883* | (2022.01) |
| *A61B 17/00* | (2006.01) |

(52) U.S. Cl.
CPC .............. *G06F 3/013* (2013.01); *G06F 3/017* (2013.01); *G06F 3/033* (2013.01); *G06F 3/0488* (2013.01); *G06F 3/04883* (2013.01); *A61B 2017/00207* (2013.01); *A61B 2017/00216* (2013.01); *G06F 2203/0383* (2013.01)

(56) References Cited

U.S. PATENT DOCUMENTS

| | | | |
|---|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,155,787 B2 | 4/2012 | Chalubert et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,515,576 B2 | 8/2013 | Lipow et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |

(56)                    References Cited

U.S. PATENT DOCUMENTS

| | | | |
|---|---|---|---|
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,682,489 B2 | 3/2014 | Itkowitz et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,880,223 B2 | 11/2014 | Raj et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,935,003 B2 | 1/2015 | Itkowitz et al. |
| 8,944,070 B2 | 2/2015 | Guthart |
| 8,989,903 B2 | 3/2015 | Weir et al. |
| 8,996,173 B2 | 3/2015 | Itkowitz et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,517,109 B2 | 12/2016 | Maeda et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,606,584 B1 | 3/2017 | Fram |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,973 B2 * | 2/2018 | Olson .................... A61B 34/30 |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |

(56) References Cited

U.S. PATENT DOCUMENTS

| | | | |
|---|---|---|---|
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,253,323 B2 | 2/2022 | Hughes et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,612,446 B2 | 3/2023 | Ramadorai | |
| 12,369,986 B2* | 7/2025 | DiMaio | G16H 40/63 |
| 2004/0243147 A1 | 12/2004 | Lipow | |
| 2005/0206583 A1 | 9/2005 | Lemelson et al. | |
| 2006/0100642 A1 | 5/2006 | Yang et al. | |
| 2006/0258938 A1 | 11/2006 | Hoffman et al. | |
| 2007/0265638 A1 | 11/2007 | Lipow et al. | |
| 2009/0248036 A1 | 10/2009 | Hoffman et al. | |
| 2010/0174410 A1 | 7/2010 | Greer et al. | |
| 2011/0110560 A1* | 5/2011 | Adhikari | G06F 3/017 |
| | | | 382/103 |
| 2011/0118752 A1 | 5/2011 | Itkowitz et al. | |
| 2011/0181510 A1 | 7/2011 | Hakala et al. | |
| 2012/0071891 A1 | 3/2012 | Itkowitz et al. | |
| 2012/0116416 A1 | 5/2012 | Neff et al. | |
| 2013/0211597 A1 | 8/2013 | Sommerville | |
| 2014/0018819 A1 | 1/2014 | Raj et al. | |
| 2014/0194896 A1 | 7/2014 | Frimer et al. | |
| 2014/0272866 A1* | 9/2014 | Kim | G09B 23/28 |
| | | | 434/262 |
| 2014/0276394 A1 | 9/2014 | Wong et al. | |
| 2015/0157411 A1 | 6/2015 | Choi | |
| 2015/0173837 A1 | 6/2015 | Barnett | |
| 2015/0366156 A1 | 12/2015 | Holmström et al. | |
| 2016/0228203 A1 | 8/2016 | Yamanaka et al. | |
| 2016/0235489 A1 | 8/2016 | Gombert et al. | |
| 2016/0310228 A1 | 10/2016 | Maeda et al. | |
| 2016/0346930 A1 | 12/2016 | Hares | |
| 2017/0000575 A1 | 1/2017 | Griffiths et al. | |
| 2017/0042730 A1 | 2/2017 | He et al. | |
| 2017/0156805 A1* | 6/2017 | Taylor | B25J 15/0466 |
| 2017/0172674 A1* | 6/2017 | Hanuschik | A61B 34/30 |
| 2017/0172675 A1 | 6/2017 | Jarc et al. | |
| 2017/0180720 A1 | 6/2017 | Jarc | |
| 2017/0189126 A1 | 7/2017 | Weir | |
| 2017/0189127 A1 | 7/2017 | Weir | |
| 2017/0189131 A1 | 7/2017 | Weir | |
| 2018/0049829 A1 | 2/2018 | Yates et al. | |
| 2018/0132833 A1 | 5/2018 | Gotlib | |
| 2018/0185104 A1* | 7/2018 | Olson | A61B 34/30 |
| 2019/0201137 A1 | 7/2019 | Shelton, IV et al. | |
| 2019/0206565 A1 | 7/2019 | Shelton, IV | |
| 2019/0231459 A1* | 8/2019 | Mustufa | A61B 34/25 |
| 2019/0290374 A1 | 9/2019 | Ramadorai | |
| 2019/0328468 A1 | 10/2019 | Schena et al. | |
| 2025/0318883 A1* | 10/2025 | Dimaio | G06T 19/006 |

FOREIGN PATENT DOCUMENTS

| | | |
|---|---|---|
| CN | 202726918 U | 2/2013 |
| CN | 103149935 A | 6/2013 |
| CN | 104688347 A | 6/2015 |
| CN | 105593787 A | 5/2016 |
| EP | 2142133 A2 | 1/2010 |
| KR | 10-2013-0051818 A | 5/2013 |
| WO | 2012044334 A2 | 4/2012 |
| WO | 2012149446 A2 | 11/2012 |
| WO | 2015143067 A1 | 9/2015 |
| WO | 2015143073 A1 | 9/2015 |

OTHER PUBLICATIONS

International Search Report and Written Opinion corresponding to counterpart Int'l Appln No. PCT/US17/035576 dated Sep. 7, 2017.
Partial European Search Report dated Jan. 3, 2020 corresponding to counterpart Patent Application EP 17807527.1.
Chinese First Office Action dated Feb. 20, 2021 corresponding to counterpart Patent Application CN 201780032069.4.
Chinese Second Office Action dated Sep. 14, 2021 corresponding to counterpart Patent Application CN 201780032069.4.
Tobii, e-book, tech.tobii.com. Copyright 2021, Tobii AB, "5 Ways Next-Generation Surgical Robotics Will Leverage Attention to Enhance Care", pp. 1/12-12/12.

(56)  References Cited

OTHER PUBLICATIONS

Tobii, Tobii White Paper, tech.tobii.com., May 2020, Version 1.0, "Why Next-Generation Surgical Systems Will Include Eye Tracking", pp. 1/15-15/15.
European Examination Report dated Feb. 14, 2024 corresponding to counterpart European Patent Application No. 17807527.1 (7 pages).

* cited by examiner

400

500

600

DISPLAY MANIPULATOR AND ENVIRONMENT REPRESENTATIONS — 602

GESTURE DETECTED INDICATING SELECTION OF REPRESENTATION? — 604

NO

YES

INDICATE SELECTION OF REPRESENTED LOCATION — 606

MOVE NON-SELECTED MANIPULATOR OUT OF SELECTED LOCATION — 610

MOVE SELECTED MANIPULATOR TO SELECTED LOCATION — 608

900

TRANSMIT ELECTRIC FIELD OR WAVES — 902

DETECT CHANGE IN ELECTRIC FIELD OR WAVES — 904

IDENTIFY GESTURE, IN RESPONSE TO DETECTED CHANGE — 906

ACTUATE MANIPULATOR OR INSTRUMENT BASED ON DETECTED GESTURE — 908

SYSTEMS, METHODS, AND COMPUTER-READABLE PROGRAM PRODUCTS FOR CONTROLLING A ROBOTICALLY DELIVERED MANIPULATOR

CROSS-REFERENCE TO RELATED APPLICATIONS

This application is a Continuation Application which claims the benefit of and priority to U.S. patent application Ser. No. 16/306,605, filed Dec. 3, 2018, which is a U.S. National Stage Application filed under 35 U.S.C. § 371(a) of International Patent Application Serial No. PCT/US2017/035576, filed Jun. 2, 2017, which claims the benefit of and priority to U.S. Provisional Patent Application Ser. No. 62/345,054, filed Jun. 3, 2016, the entire disclosure of which is incorporated by reference herein.

BACKGROUND

Robotic surgical systems are increasingly being used in minimally invasive medical procedures. Typically, robotic surgical systems include a surgeon console located remote from one or more robotic arms to which surgical instruments and/or cameras are coupled. The surgeon console may be located on another side of the operating room from the robotic arms, in another room, or in another building, and includes input handles or other input devices for receiving inputs from a surgeon. The inputs are communicated to a central controller, which translates the inputs into commands for manipulating the robotic arms in the vicinity of the patient.

Multiple instruments may be used during the course of a surgical procedure. As such, the robotic surgical system may include different instruments coupled to each robotic arm thereby allowing the surgeon to select an input handle or input device corresponding to a desired instrument for use. In some instances, the surgeon may choose to employ an instrument that is not already coupled to one of the robotic arms. In such case, the surgeon may indicate verbally to a bedside assistant a desire to exchange one attached surgical instrument for another. In response to the verbal direction, the bedside assistant physically performs the instrument exchange. In many cases, communication from the surgeon to the bedside assistant is made over an intercommunication system.

Although the current systems and methods for performing robotic surgical procedures are functional, they may be improved. For example, due to various influences that may be present within the operating room, communication between the surgeon and the bedside assistant may become difficult from time to time. In some cases, noises from various status monitors present within the operating room, and/or other audible distractions may cause the bedside assistant to have difficulty hearing the surgeon's communication. The bedside assistant may inadvertently attach and then replace a tool on the robotic arm that was not requested by the surgeon, and the attachment and replacement may be counted toward and/or decremented from the tool's useful life. As a result, the hospital may incur an unwarranted usage fee, which may ultimately be passed through to patients. Additionally, the surgeon may prefer that an instrument be positioned in a particular manner, which may be challenging to convey verbally.

SUMMARY

Accordingly, there is a need for robotic surgical systems and methods that improve procedure efficiencies as well as safety. Additionally, there is a need for robotic surgical systems that allow the surgeon to have improved control over what actions are taken at the patient's bedside and how the actions are implemented.

In accordance with an aspect of the present disclosure, a robotic surgical system is provided that includes a robotic surgical system is provided including a robotic manipulator having a base and a surgical instrument holder configured to move relative to the base, a surgical instrument removably coupled to the surgical instrument holder, a user interface configured to present information related to at least one of the robotic manipulator or the surgical instrument, a gesture detection sensor configured to detect a gesture made by a user, and a controller in communication with the robotic manipulator, the surgical instrument, the user interface, and the gesture detection sensor. The controller includes one or more processors and one or more memories having instructions stored thereon which when executed by the one or more processors cause the one or more processor to provide one or more commands to actuate the robotic manipulator in a predetermined manner corresponding to the detected gesture.

In another aspect of the present disclosure, the user interface is a touch screen, the gesture detection sensor is a touch sensor, the presented information is a graphical representation of the surgical instrument, and the one or more memories have stored thereon, further instructions which when executed by the one or more processors cause the one or more processors to determine whether or not a gesture has been detected on the touch screen over the graphical representation of the surgical instrument presented thereon, and in response to a determination that a gesture has been detected, provide the one or more commands to actuate the robotic manipulator in the predetermined manner corresponding to the detected gesture.

In still another aspect of the present disclosure, the user interface is a touch screen, the gesture detection sensor is a touch sensor, the presented information is a graphical representation of the robotic manipulator, and the one or more memories have stored thereon, further instructions which when executed by the one or more processors cause the one or more processors to determine whether or not a gesture has been detected on the touch screen over the graphical representation of the surgical instrument presented thereon, and in response to a determination that a gesture has been detected, provide the one or more commands to actuate the robotic manipulator in the predetermined manner corresponding to the detected gesture.

In another aspect of the present disclosure, the user interface is a display, the gesture detection sensor is a camera sensor, the information presented on the display is a graphical representation of the surgical instrument, and the one or more memories have stored thereon, further instructions which when executed by the one or more processors cause the one or more processors to determine whether or not a gesture has been detected by the camera sensor, and in response to a determination that a gesture has been detected, provide the one or more commands to actuate the robotic manipulator in the predetermined manner corresponding to the detected gesture.

In still another aspect of the present disclosure, the gesture detection sensor is an electric field-based sensor configured to generate an electric field. The one or more memories have stored thereon, further instructions which when executed by the one or more processors cause the one or more processors to determine whether or not a gesture has been detected by the electric field-based sensor by receiving a transmission of a change in the electric field generated by the electric field-based sensor, identify a gesture, based on the change in the electric field, and provide the one or more commands to actuate the robotic manipulator in a predetermined manner corresponding to the identified gesture.

In still another aspect of the present disclosure, the gesture detection sensor is a radar interaction sensor configured to transmit electromagnetic waves having a predetermined frequency. The one or more memories have stored thereon, further instructions which when executed by the one or more processors cause the one or more processors to determine whether or not a gesture has been detected by the radar interaction sensor by receiving a transmission of a change in one or more of an amplitude or a signal of the transmitted electromagnetic waves generated by the radar interaction sensor, identify a gesture, based on the change in the one or more of an amplitude or a signal of the transmitted electromagnetic waves, and provide the one or more commands to actuate the robotic manipulator in a predetermined manner corresponding to the identified gesture.

In still another aspect of the present disclosure, a user image capture device coupled to the controller and configured to capture images of the user. The one or more memories have stored thereon, further instructions which when executed by the one or more processors cause the one or more processors to receive the captured images of the user, track one or both of the eyes of the user, identify a selection, based on the tracked one or both of the eyes of the user, and provide the one or more commands to actuate the robotic manipulator in a predetermined manner corresponding to the identified selection.

According to another aspect of the present disclosure, a method is provided for controlling a robotic surgical system. The method includes presenting information related to at least one of a robotic manipulator or a surgical instrument, the robotic manipulator having a base and a surgical instrument holder configured to move relative to the base, and the surgical instrument being removably coupled to the surgical instrument holder, detecting a gesture made by a user representing a desired movement of the robotic manipulator, and actuating the robotic manipulator in a predetermined manner corresponding to the detected gesture.

In another aspect of the present disclosure, the user interface is a touch screen, the gesture detection sensor is a touchscreen sensor, the presented information is a graphical representation of the surgical instrument, and the method further includes determining whether or not a gesture has been detected on the touch screen over the graphical representation of the surgical instrument presented thereon, and in response to a determination that a gesture has been detected, actuating the robotic manipulator in a predetermined manner corresponding to the detected gesture.

In still another aspect of the present disclosure, the user interface is a touch screen, the gesture detection sensor is a touchscreen sensor, the presented information is a graphical representation of the robotic manipulator, and the method further includes determining whether or not a gesture has been detected on the touch screen over the graphical representation of the surgical instrument presented thereon, and in response to a determination that a gesture has been detected, actuating the robotic manipulator in the predetermined manner corresponding to the detected gesture.

In still another aspect of the present disclosure, the user interface is a display, the gesture detection sensor is a camera sensor, the information presented on the display is a graphical representation of the surgical instrument, and the method further includes determining whether or not a gesture has been detected by the camera sensor, and in response to a determination that a gesture has been detected, actuating the robotic manipulator in the predetermined manner corresponding to the detected gesture.

In another aspect of the present disclosure, the gesture detection sensor is an electric field-based sensor configured to generate an electric field, and the method further comprises determining whether or not a gesture has been detected by the electric field-based sensor by receiving a transmission of a change in the electric field generated by the electric field-based sensor, identifying a gesture, based on the change in the electric field, and actuating the robotic manipulator in a predetermined manner corresponding to the identified gesture.

In still another aspect of the present disclosure, the gesture detection sensor is a radar interaction sensor configured to transmit electromagnetic waves having a predetermined frequency, and the method further comprises determining whether or not a gesture has been detected by the radar interaction sensor by receiving a transmission of a change in one or more of an amplitude or a signal of the transmitted electromagnetic waves generated by the radar interaction sensor, identifying a gesture, based on the change in the one or more of an amplitude or a signal of the transmitted electromagnetic waves, and actuating the robotic manipulator in a predetermined manner corresponding to the identified gesture.

In still yet another aspect of the present disclosure, a user image capture device is coupled to the controller and configured to capture images of the user, and the method further comprises receiving the captured images of the user, tracking one or both of the eyes of the user, identifying a selection, based on the tracked one or both of the eyes of the user, and actuating the robotic manipulator in a predetermined manner corresponding to the identified selection.

According to another aspect of the present disclosure, a non-transitory computer-readable medium is included that stores instruction that, when executed by a computer, cause the computer to present information related to at least one of a robotic manipulator or a surgical instrument, the robotic manipulator having a base and a surgical instrument holder configured to move relative to the base, and the surgical instrument being removably coupled to the surgical instrument holder, detect a gesture made by a user representing a desired movement of the robotic manipulator, and actuate the robotic manipulator in a predetermined manner corresponding to the detected gesture.

In accordance with another aspect of the present disclosure, a robotic surgical system is provided including a console, a robotic arm, and a controller. The console includes a user interface configured to display one or more surgical instrument representations and to sense a gesture within a predetermined distance of one of the one or more surgical instrument representations. The robotic arm has a distal end configured to selectively couple to and decouple from a surgical instrument. The controller is in communication with the robotic arm and the console and includes one or more processors and one or more memories having instructions stored thereon which, when executed by the one or more processors, cause the one or more processors to, in response to detecting the gesture indicating the selection of one of the one or more surgical instrument representations, detect a location of a surgical instrument corresponding to the selected one of the one or more surgical instrument representations, and determine whether the corresponding surgical instrument is coupled to the distal end of the robotic arm.

In another aspect of the present disclosure, the robotic surgical system further includes the user interface having a touchscreen and a sensor.

In another aspect of the present disclosure, the robotic surgical system further includes the user interface having a display and a sensor.

In still another aspect of the present disclosure, the robotic surgical system further includes the memory of the controller having instructions that, when executed by the processor, causes the processor to in response to a determination that the corresponding surgical instrument is not coupled to the distal end of the robotic arm cause the robotic arm to move to the detected location.

In another aspect of the present disclosure, the robotic surgical system includes memory of the controller which further includes instructions that, when executed by the processor, causes the processor to in response to a determination that the corresponding surgical instrument is coupled to the distal end of the robotic arm cause the robotic arm to move to a selected location.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION

Figure 1:
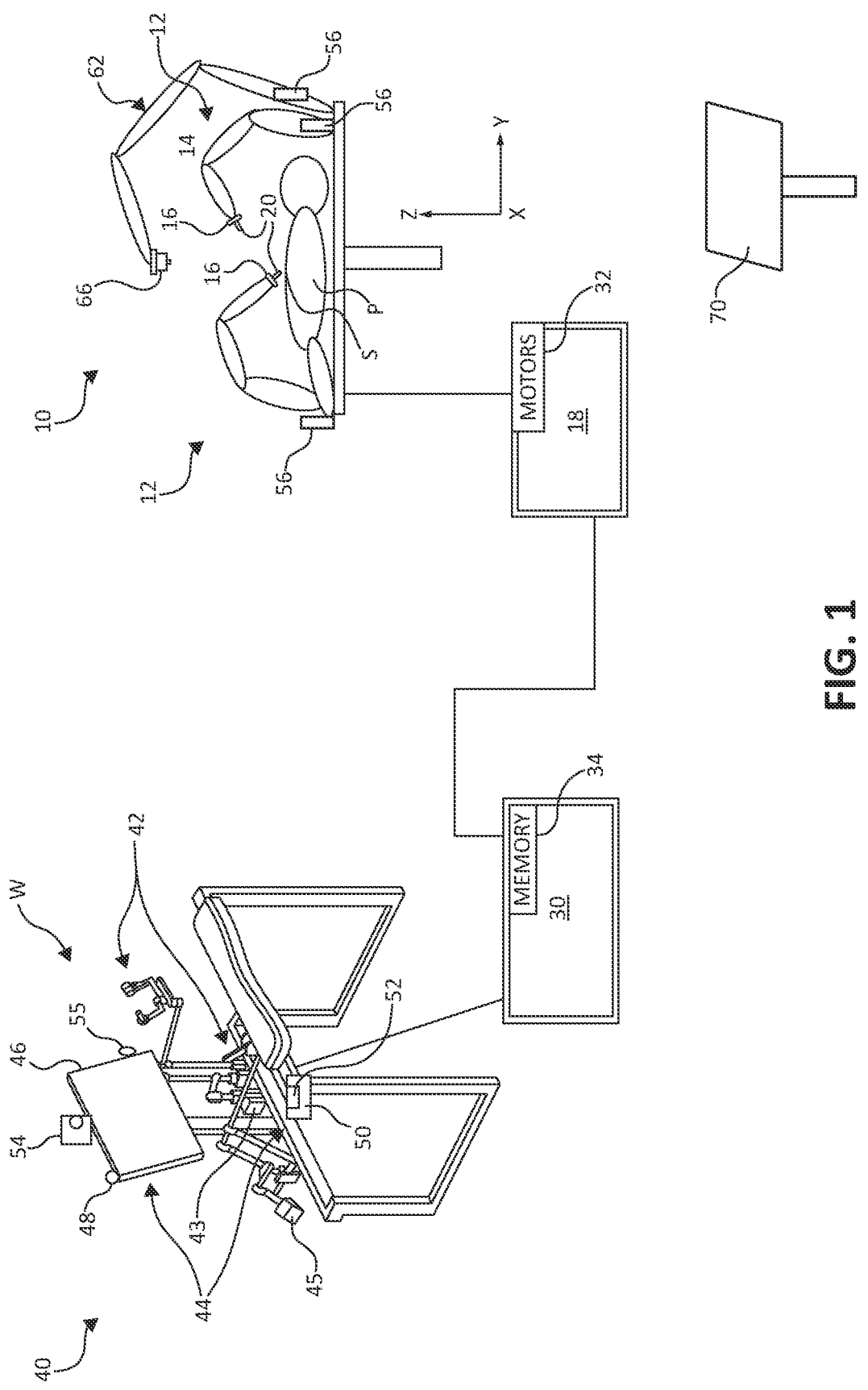
FIG. 1 is a schematic illustration of a medical work station and operating console in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is farthest from the patient and the term "distal" refers to the portion of the device or component thereof that is closest to the patient.

With reference to FIG. 1, a robotic surgical system 10 is provided, which is configured for use on a patient "P" lying on a patient table for the performance of a minimally invasive surgical operation. In accordance with an embodiment, the robotic surgical system 10 generally includes a plurality of robotic manipulators 12 configured to receive commands from a controller 30 for manipulating one or more of the robotic manipulators 12 in response to an input received at a remotely-located surgeon console 40.

Each of the robotic manipulators 12 is made up of a plurality of members connected through joints coupled to and extending from a base 18. Although the base 18 is illustrated schematically as a single location, it will be appreciated that the base 18 may be made up of a plurality of locations from which each robotic manipulator 12 extends. For example, the base 18 may be made up of a plurality of movable carts. In an embodiment, connected to a distal end of each robotic manipulator 12 is a surgical assembly 14, which includes a surgical instrument holder 16 that is configured to removably couple with a surgical instrument 20. Each robotic manipulator 12 may include a surgical instrument 20 configured for a different purpose. For example, one robotic manipulator 12 may include a surgical instrument including a grasping jaw instrument 20, while another robotic manipulator 12 may include a surgical instrument including scissors. Other suitable instruments 20 include, but are not limited to, staplers, clip appliers, suture passers, spatulas, and the like.

Although two robotic manipulators 12 are depicted, the surgical system 10 may include more than two robotic manipulators 12. In this regard, the additional robotic manipulators (not shown) are likewise connected to the controller 30 and are telemanipulatable via the console 40. Accordingly, one or more additional surgical assemblies 14, surgical instrument holders 16, and/or surgical instruments 20 may also be attached to the additional robotic manipulators. In another embodiment, one or more of the robotic manipulators 12 includes an imaging device 66 positioned over the surgical site "S", in the surgical site "S" (not shown) or the like. The imaging devices 66 may capture visual images, infra-red images, ultrasound images, X-ray images, thermal images, and/or any other known real-time images of the surgical site "S". The imaging devices transmit captured imaging data to the controller 30 which creates three-dimensional images of the surgical site "S" in real-time from the imaging data and transmits the three-dimensional images to a display device 46 for display. In another embodiment, the displayed images are two-dimensional renderings of the data captured by the imaging devices.

The robotic manipulators 12 may be driven by electric drives (not shown) that are connected to the controller 30. According to an embodiment, the controller 30 is configured to activate drives, for example, via a computer program, such that the robotic manipulators 12 and the surgical assemblies 14, surgical instrument holders 16, and/or surgical instruments 20 corresponding to the robotic manipulators 12, execute a desired movement received through the console 40. The controller 30 may also be configured to regulate movement of the robotic manipulators 12 and/or the drives.

In an embodiment, one or more gesture detection sensors 56 may be included on or adjacent one or more of the robotic manipulators 12 (such as in the form of a wearable for a bedside assistant or clinician or on a transportable device).

For example, one or more of the gesture detection sensors 56 may include electric field-based gesture detection sensors configured to output a circumambient electric field, which provides a scanning region in which inputs or changes to the electric field may be detected. The detected inputs are transmitted to the controller 30, which may be trainable to recognize or may have access to a database of stored patterns associated with the detected inputs where the patterns each correspond to commands to move the robotic manipulators 12 in a predetermined manner. In another embodiment, one or more of the gesture detection sensors 56 may include radar interaction sensors, which may be configured to transmit waves in a particular spectrum including radio frequency at a target, and reflected waves are then received by the sensor and provided to the controller 30. Similar to the controller 30 configured to operate with electric field-based gesture detection sensors, the controller 30 here may be trained to recognize or have access to a database storing patterns associated with inputs, where the patterns correspond to commands. An example of an electric field-based gesture sensor includes the GestIC® technology available through Microchip Technology Inc. of Chandler, Arizona, and an example of a radar interaction sensor includes the Project Soli™ sensor available through Google, Inc. of Mountain View, California. In another embodiment, alternative sensors may be implemented.

The controller 30 may control a plurality of motors 32 with each motor configured to drive a pushing or a pulling of one or more cables such as cables (not shown) coupled to the surgical instrument 20. In use, as these cables are pushed and/or pulled, the one or more cables effect operation and/or movement of the surgical instruments 20. The controller 30 coordinates the activation of the various motors 32 to coordinate a pushing or a pulling motion of one or more cables in order to coordinate an operation and/or movement of one or more surgical instrument 20. In an embodiment, each motor 32 is configured to actuate a drive rod or a lever arm to effect operation and/or movement of surgical instruments 20 in addition to, or instead of one or more cables.

The controller 30 includes any suitable logic control circuit adapted to perform calculations and/or operate according to a set of instructions. The controller 30 can be configured to communicate with a remote system (not shown) either via a wireless (e.g., Wi-Fi, Bluetooth, LTE, etc.) and/or wired connection. The remote system can include data, instructions and/or information related to the various components, algorithms, and/or operations of console 40. The remote system can include any suitable electronic service, database, platform, cloud, or the like. The controller 30 may include a central processing unit operably connected to memory. The memory may include transitory type memory (e.g., RAM) and/or non-transitory type memory (e.g., flash media, disk media, etc.). In some embodiments, the memory is part of, and/or operably coupled to, the remote system.

The controller 30 can include a plurality of inputs and outputs for interfacing with the components of the console 40 and/or the robotic arm 12, such as through a driver circuit. The controller 30 can be configured to receive input signals from the console 40, or in an embodiment, from the gesture detection sensors 56 disposed on or adjacent one or more of the robotic arms 12 and/or to generate output signals to control one or more of the various components (e.g., one or more motors) based on the input signals. The output signals can include, and/or can be based upon, algorithmic instructions which may be pre-programmed and/or input by a user. The controller 30 can be configured to accept a plurality of user inputs from a user interface (e.g., switches, buttons, touch screen, etc. of operating the console 40) which may be coupled to remote system.

A memory 34 can be directly and/or indirectly coupled to the controller 30 to store instructions and/or databases including pre-operative data from living being(s) and/or anatomical atlas(es). The memory 34 can be part of, and/or or operatively coupled to, the remote system.

To provide the input to the controller 30 via the surgeon console 40, the surgeon console 40 includes various input devices. In an embodiment, the surgeon console 40 includes input handles 42 or input pedals 45 configured to be manipulated by the clinician through actuation. In particular, the clinician uses his or her hands to grip and move the input handles 42 and the movement of the input handles 42 are translated via the controller 30 to thereby provide a corresponding movement to the robotic manipulators 12 and/or surgical instruments 20. The clinician steps on the input pedals 45 to provide a selection to provide further controls of the robotic manipulators 12.

The surgeon console 40 further includes a user interface system 44 to provide additional mechanisms by which the clinician can control the robotic manipulators 12. According to an embodiment, the user interface system 44 includes mechanisms to allow the clinician to select a robotic manipulator 12 to use, to more easily cause movement of the robotic manipulator 12, to identify surgical instruments 20 that are not already in use, and/or to select use of the robotic manipulators 12 on which they may be coupled. The user interface system 44 is also configured to simplify the exchange of surgical instruments 20 that may not already be coupled to a robotic manipulator 12, in an embodiment. In another embodiment, the user interface system 44 is configured to detect gestures and to translate the detected gestures into movement of the robotic manipulators 12. In this regard, the user interface system 44 includes one or more of a display 46, gesture detection sensors 48, a touch screen 50 including embedded sensors 52, a user image capture device 54, and/or a microphone 55.

The display 46 is set up to display two- or three-dimensional images such as information about at least one of the robotic manipulator 12 and the surgical instrument 20. In an embodiment in which three-dimensional images are provided, the display 46 is configured to provide the three-dimensional images for viewing either with or without specialized viewing lenses provided, for example, in the form of glasses, head sets or other suitable configuration. The display 46 operates with the one or more gesture detection sensors 48 to detect a gesture or movement provided by the clinician. To detect the gestures or movements, the gesture detection sensors 48 may include camera sensors, image sensors, motion sensors, optical sensors, heat sensors, infrared sensors, sensors similar to those described above with respect to the gesture detection sensors 56 of the manipulator 12, any other type of sensor capable of detecting movement, and/or any combination thereof. The gesture detection sensors 48 are mounted to or adjacent the display 46, such as along a top of the display 46 as illustrated in FIG. 1, in an embodiment. Alternatively, the gesture detection sensors 48 are mounted on or adjacent a side or on a bottom of the display 46. In an embodiment, more than one of the gesture detection sensors 48 are mounted at multiple locations around or on the display 46. In still another embodiment, the gesture detection sensors 48 may be disposed on a wearable device (not shown) that may be temporarily attached to the clinician, for example, on a hand, as a glove or other hand-fitting configuration.

The touch screen 50, if included, is disposed on the work station console 40 at a location that is relatively convenient for the clinician to access, for example, within arms' reach. Thus, when positioned to operate the input handles 42, the surgeon is also able to manipulate the touch screen 50. In an embodiment, the touch screen 50 is coupled to a frame 43 of the work station console 40, such as a portion of the frame 43 supporting an arm rest 45, as illustrated in FIG. 1, and may be adjustable in height or proximity to the clinician's position. In another embodiment, the touch screen 50 is mounted to a moveable stand that is separate from the frame 43 and is positioned adjacent the arm rest 45. Similarly, the touch screen 50 mounted to the moveable stand can be repositioned closer to or farther away from the clinician's position or adjusted in height, as desired. The touch screen 50 is configured to present information about at least one of the robotic manipulators 12 and the surgical instruments 20. The touch screen 50 includes sensors 52 that are embedded therewithin for detecting gestures made over or on the touch screen 50. Suitable sensors capable of detecting gestures include touch sensors, capacitive sensors, optical sensors, electromagnetic field change sensors, localized radar sensing, and the like. It will be appreciated that the touch screen 50 and sensors 52 are configured in any one of numerous suitable manners for detecting a gesture over or on a surface of the touch screen 50.

The user image capture device 54, if included, is configured to capture images of the clinician at the surgeon console 40 for the purposes of eye-tracking. In accordance with an embodiment, the user image capture device 54 is mounted to the display device 46 or at another location to allow the user image capture device 54 to be directed at the clinician during system operation. The user image capture device 54 may include one or more filters for the detection of the user's eyes, in an embodiment.

The microphone 55, if included, is configured to capture voice and/or other sounds at the surgeon console 40 and is mounted to the display device 46, or attached to another location, such as a stand (not shown), a headset (not shown), other wearable (not shown) and the like.

Figure 2:
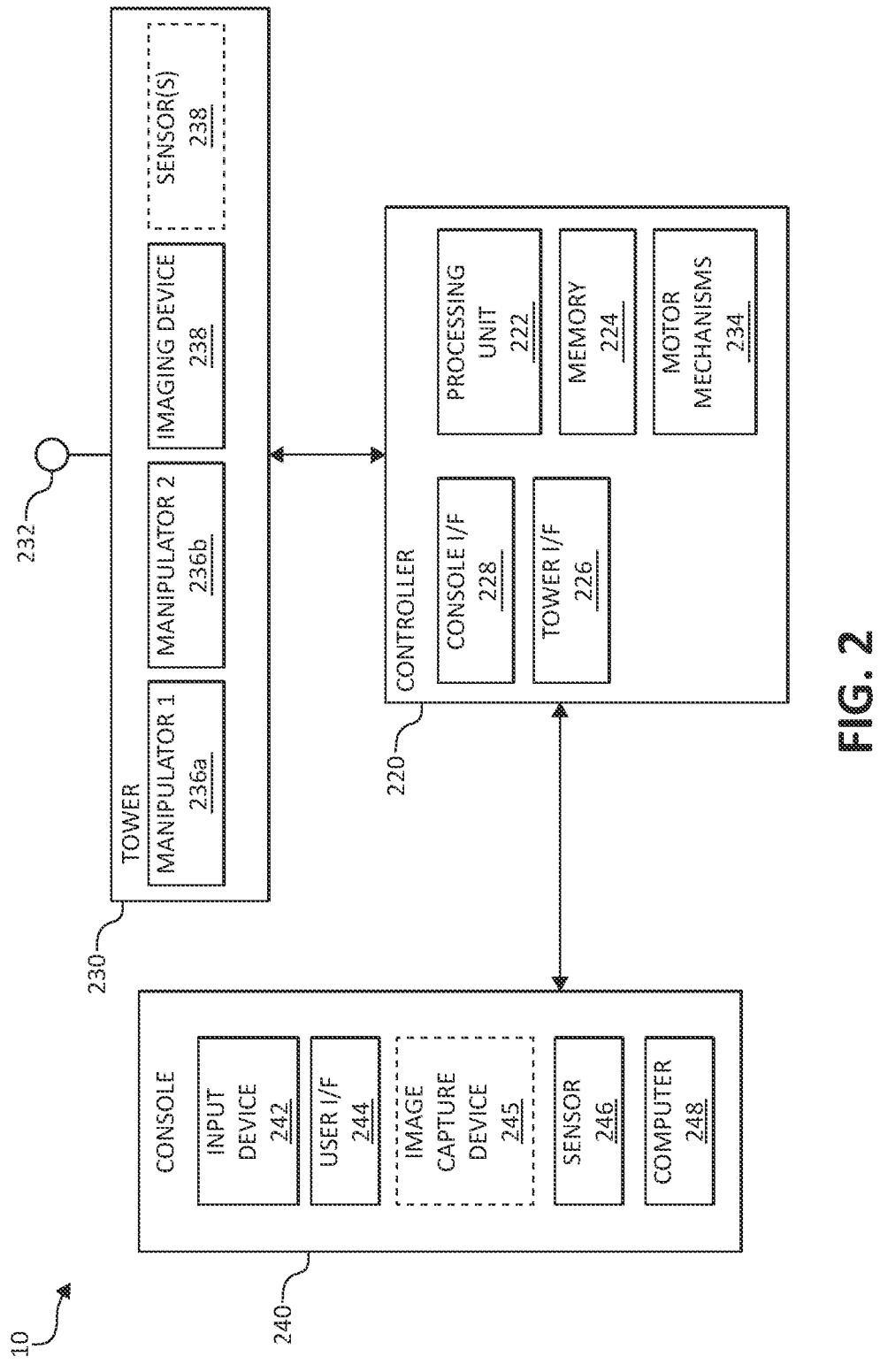
FIG. 2 is a functional block diagram of the system architecture for controlling the multi-input robotic surgical system of FIG. 1.

FIG. 2 is simplified block diagram of the robotic surgical system 10 of FIG. 1. The robotic surgical system 10 includes a controller 220, a tower 230, and one or more consoles 240. The controller 220 is configured to communicate with the tower 230 to thereby provide instructions for operation, in response to input received from one of the consoles 240.

The controller 230 generally includes a processing unit 222, a memory 224, a tower interface 226, and a console interface 228. The processing unit 222, in particular by means of a computer program stored in the memory 224, functions in such a way to cause components of the tower 230 to execute a desired movement according to a movement defined by input devices 242 of the console 240. In this regard, the processing unit 222 includes any suitable logic control circuit adapted to perform calculations and/or operate according to a set of instructions. The processing unit 222 may include one or more processing devices, such as a microprocessor-type of processing device or other physical device capable of executing instructions stored in the memory 224 and/or processing data. The memory 224 may include transitory type memory (e.g., RAM) and/or non-transitory type memory (e.g., flash media, disk media, etc.). The tower interface 226 and consoles interface 228 communicate with the tower 230 and console 240, respectively, either wirelessly (e.g., Wi-Fi, Bluetooth, LTE, etc.) and/or via wired configurations. Although depicted as separate modules, the interfaces 232, 234 may be a single component in other embodiments.

The tower 230 includes a communications interface 232 configured to receive communications and/or data from the tower interface 226 for manipulating motor mechanisms 234 to thereby move manipulators 236a, 236b. In accordance with an embodiment, the motor mechanisms 234 are configured to, in response to instructions from the processing unit 222, receive an application of current for mechanical manipulation of cables (not shown) which are attached to the manipulators 236a, 236b to cause a desired movement of a selected one of the manipulator 236a, 236b and/or an instrument coupled to a manipulator 236a, 236b. The tower 230 also includes an imaging device 238, which captures real-time images and transmits data representing the images to the controller 230 via the communications interface 232, and one or more sensors 250, which detects gestures made by a bedside assistant or user and transmits signals representing the detected gestures to the computer 248.

To further manipulate the devices of the tower 230, the console 240 has an input device 242, a user interface 244, an image capture device 245, sensors 246, and a computer 248. The input device 242 is coupled to the computer 246 and is used by the clinician to provide an input. In this regard, the input device 242 may be a handle or pedal, or other computer accessory, such as a keyboard, joystick, mouse, button, trackball or other component. In addition to the aforementioned devices, the input device 242 may also include a microphone or other device configured to receive sound input. The user interface 244 displays images or other data received from the controller 220 to thereby communicate the data to the clinician and operates in conjunction with the sensors 246, which detect gestures made by the clinician and sends signals representing the detected gestures to the computer 248. The image capture device 245, if included, captures images of the clinician at the console 240 and provides the captured images, either as still images or as a video stream, to the computer 248. The computer 248 processes the images or video for the purposes of eye-tracking. The computer 248 includes a processing unit and memory, which includes data, instructions and/or information related to the various components, algorithms, and/or operations of the tower 230 and can operate using any suitable electronic service, database, platform, cloud, or the like.

Figure 3:
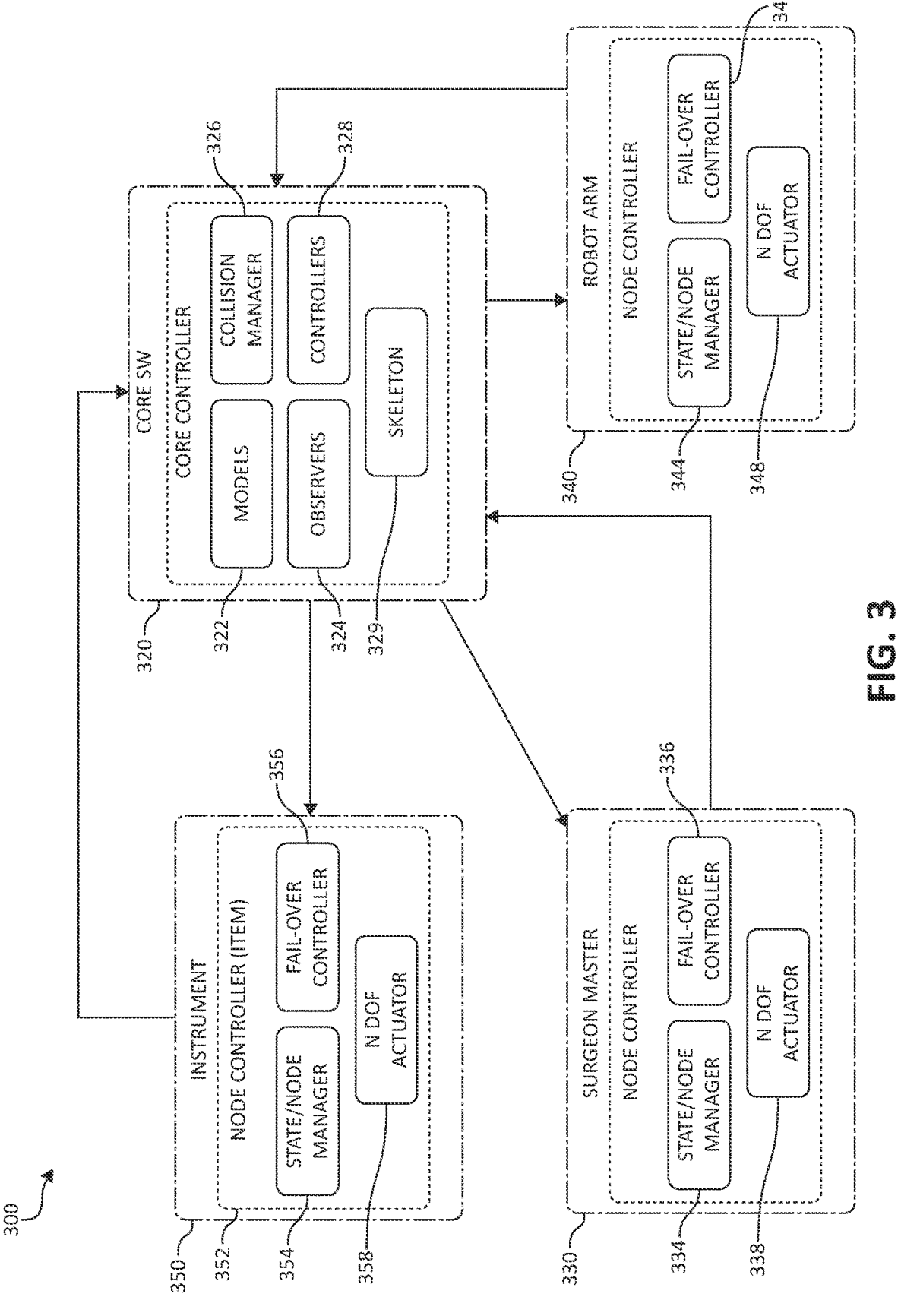
FIG. 3 is a block diagram of control components, of the present disclosure, for controlling the robotic surgical system of FIG. 1.
Figure 4:
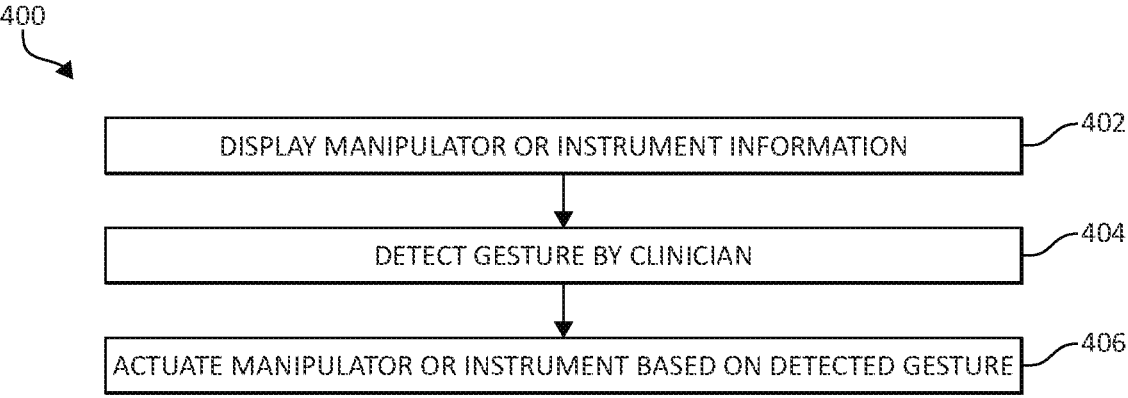
FIG. 4 is a flow diagram of a method of controlling the multi-input robotic surgical system, in accordance with an embodiment.

FIG. 3 is a simplified functional block diagram of a system architecture 300 of the robotic surgical system 10 of FIG. 1. The system architecture 300 includes a core module 320, a surgeon master module 330, a robot arm module 340, and an instrument module 350. The core module 320 serves as a central controller for the robotic surgical system 10 and coordinates operations of all of the other modules 330, 340, 350. For example, the core module 320 maps control devices to the manipulators 12, determines current status, performs all kinematics and frame transformations, and relays resulting movement commands. In this regard, the core module 320 receives and analyzes data from each of the other modules 330, 340, 350 in order to provide instructions or commands to the other modules 330, 340, 350 for execution within the robotic surgical system 10. Although depicted as separate modules, one or more of the modules 320, 330, 340, and 350 are a single component in other embodiments.

The core module 320 includes models 322, observers 324, a collision manager 326, controllers 328, and a skeleton 329. The models 322 include units that provide abstracted representations (base classes) for controlled components, such as the motors 32 and/or the manipulators 12. The observers 324 create state estimates based on input and output signals received from the other modules 330, 340, 350. The collision manager 326 prevents collisions between components that have been registered within the system 10. The skeleton 329 tracks the system 10 from a kinematic and dynamics point of view. For example, the kinematics item may be implemented either as forward or inverse kinematics, in an embodiment. The dynamics item may be implemented as algorithms used to model dynamics of the system's components.

The surgeon master module 330 communicates with surgeon control devices at the console 40 and relays inputs received from the console 40 to the core module 320. In accordance with an embodiment, the surgeon master module 330 communicates button status and control device positions to the core module 320 and includes a node controller 332 that includes a state/mode manager 334, a fail-over controller 336, and a N degree-of-freedom ("DOF") actuator 338.

The robot arm module 340 coordinates operation of a robot arm subsystem, an arm cart subsystem, a set up arm, and an instrument subsystem in order to control movement of a corresponding manipulator 12. Although a single robot arm module 340 is included, it will be appreciated that the robot arm module 340 corresponds to and controls a single manipulator 12. As such, additional modules 340 are included in configurations in which the system 10 includes multiple manipulators 12. The robot arm module 340 includes a node controller 342, a state/mode manager 344, a fail-over controller 346, and a N degree-of-freedom ("DOF") actuator 348.

The instrument module 350 controls movement of the surgical instrument 20 (shown in FIG. 1) attached to the robotic manipulator 12. The instrument module 350 is configured to correspond to and control a single surgical instrument. Thus, in configurations in which multiple surgical instruments are included, additional instrument modules 350 are likewise included. In an embodiment, the instrument module 350 obtains and communicates data related to the position of the surgical instrument 20 relative to the one or more manipulators 12. The instrument module 350 has a node controller 352, a state/mode manager 354, a fail-over controller 356, and a N degree-of-freedom ("DOF") actuator 358.

The position data collected by the instrument module 350 is used by the core module 320 to determine the locations of each robotic manipulator 12, where the surgical instrument 20 is within the surgical site, within the operating room, and/or relative to one or more of the robotic manipulators 12. In an embodiment, the core module 320 determines whether or not to move a selected robotic manipulator 12 to the surgical site "S". In particular, when a gesture is detected, the core module 320 determines whether the detected gesture indicates a selection of a robotic manipulator 12 and, if so, provides instructions to cause the selected robotic manipulator 12 to move to a selected location. The selected location may be the surgical site "S" or a location away from the surgical site "S".

In another embodiment, the core module 320 receives inputs from the sensor 246 and determines whether to output instructions for exchanging one instrument 20 for another, based on an actual position of a selected surgical instrument 20 and a desired position of the selected surgical instrument 20 and on the received inputs. For example, when position data from the instrument module 350 indicates that the position of a first surgical instrument 20 on a first manipulator 12 is within a surgical site "S" and a gesture is detected by the sensors 246 to move the first surgical instrument 20 to another location, instructions are outputted to cause the first manipulator 12 to move out of the surgical site "S". When a gesture is detected by the sensors 246 to use a second instrument 20 coupled to a second manipulator 12, instructions are outputted to move the first manipulator 12 out of the surgical site "S" and outputted to move the second manipulator 12 in a manner to move the second instrument 20 into the surgical site "S".

In another embodiment, the core module 320 receives inputs from the sensor 250 and determines whether to output instructions to move the manipulator 12, based on the received inputs. When a gesture is detected by the sensors 250, the core module 320 identifies the gesture, based on a signal from the sensor 250 (for example, a change in an electric field in the case of an electric field-based sensor or a change in signal or frequency in the case of a radar interaction sensor), and provide the commands to actuate the robotic manipulator in a predetermined manner corresponding to the identified gesture.

In still another embodiment, the core module 320 receives inputs from the user image capture device 54 (e.g., images and/or video) and/or the microphone 55 (e.g., voice commands and/or other sounds) and processes the inputs using known algorithms. For example, the core module 320 identifies isolated features from the images, video, or sounds, and provides commands to actuate the robotic manipulator 12 or surgical instrument 20 in a predetermined manner corresponding to the identified isolated feature.

FIGS. 4-9 are flow diagrams depicting various embodiments of methods for controlling the robotic surgical system 10, based on the inputs received from the gesture detection sensors and/or the user image capture device described above.

In an embodiment, a gesture is received as an input at the surgeon console 40, for example, at the touchscreen 59 or via the gesture detection sensor 48, and the gesture is translated into commands to move one or more selected robotic manipulators 12 and/or selected surgical instruments 20 in a desired manner. In this regard, turning now to FIG. 4, an exemplary method 400 of controlling the robotic surgical system 10 is provided. In step 402, information relating to one or more of the robotic manipulators 12 and/or the surgical instruments 20 is displayed. For example, the information is presented as visual representations, such as pictorial icons or other graphical representation that correspond to one or more of the robotic manipulators 12 and/or instruments 20 or as text boxes indicating one or more of the robotic manipulators 12 and/or instruments 20. In an embodiment, the information is presented in a map form indicating the positions of the robotic manipulators 12 and/or instruments 20 relative to each other. In another embodiment, a representation of the robotic surgical system 10 and/or the operating room in which the robotic surgical system 10 is depicted and the information including the one or more of the robotic manipulators 12 and/or instruments 20 is presented in the representation. In another embodiment, the information does not indicate the positioning, and simply lists or shows icons or text boxes representing the robotic manipulators 12 and/or instruments 20. The information is presented either on the touch screen 50 or display 46.

The clinician then provides an input into the system 10 to effect a desired movement. In this regard, a gesture made by the clinician is detected at step 404. In an embodiment, the gesture from the clinician may be detected via the sensors 52 on the touch screen 50. For example, the clinician may tap an icon on the touch screen 50 to provide input indicating a desired selection. In another embodiment, the gesture from the clinician may be detected via the gesture detection sensor 48 on the display 46. In such an embodiment, a movement or gesture by the clinician over the display 46 is detected by the gesture detection sensor 48. As a result of the detection of the gesture over the display 46, commands may be provided to move an icon on the display 46 over which the gesture was made across the display 46 or commands may be provided to move a corresponding icon across the touch screen 50. In addition to detecting the gesture over the display 46, position data of the detected gesture may be obtained as the gesture is being made. For example, in accordance with an embodiment, the position data detected from the detected gesture may be represented as a set of coordinates and velocities, vector or other location and directional identifiers in space relative to a fixed location.

At step 406, the robotic manipulator 12 is actuated according to the detected gesture. In an embodiment, a comparison is made over time between an initial detection by the gesture detection sensor 48 and subsequent detections by the gesture detection sensor 48. For example, the comparison determines whether a difference between one or more selected parameters, such as distance, dwelling/pause time, and the like, is outside of a predetermined threshold range of the corresponding parameter, which may, for example, indicate that the path of the detected gesture or the end position of the detected gesture, is adjacent or within the proximity of an icon representing presented information. If not, a determination is made that the detected gesture does not correspond to a selection, and the gesture detection sensor 48 continues to detect gestures made by the clinician. When the difference is outside of one or more of the predetermined threshold ranges, then a determination is made that the detected gesture corresponds to a selection. In an embodiment in which the gestures are detected by sensors 52 on the touch screen 50, the gesture detection sensor 52 detects a presence of the clinician's hand over the touch screen 50 and may correspond the position to one of the manipulators 12 or surgical instruments 20. In a case in which the clinician's hand is maintained at the position for a duration outside of a predetermined threshold range and/or the movement of the clinician's hand is outside of a predetermined threshold range, commands are provided to actuate the robotic manipulator 12 in a predetermined manner corresponding to the detected gesture, more specifically, the selection. In another embodiment in which gestures are detected by sensors 48 in front of the display 46, the gesture detection sensor 48 detects a presence of the clinician's hand at a position, which may correspond to one of the manipulators 12 or surgical instruments 20. Similar to the previous embodiment, in a case in which the clinician's hand is maintained at the position for a duration outside of a predetermined threshold range and/or movement of the clinician's hand is outside of a predetermined threshold range, commands are provided to actuate the robotic manipulator 12 in a predetermined manner corresponding to the detected gesture. In another embodiment in which the gestures are detected by the sensor 48, actuation occurs when the position of the detected gesture in space is adjacent or within the proximity of another position in space, which when translated causes the display 46 to appear to represent presented information corresponding to the detected gesture.

Figure 5:
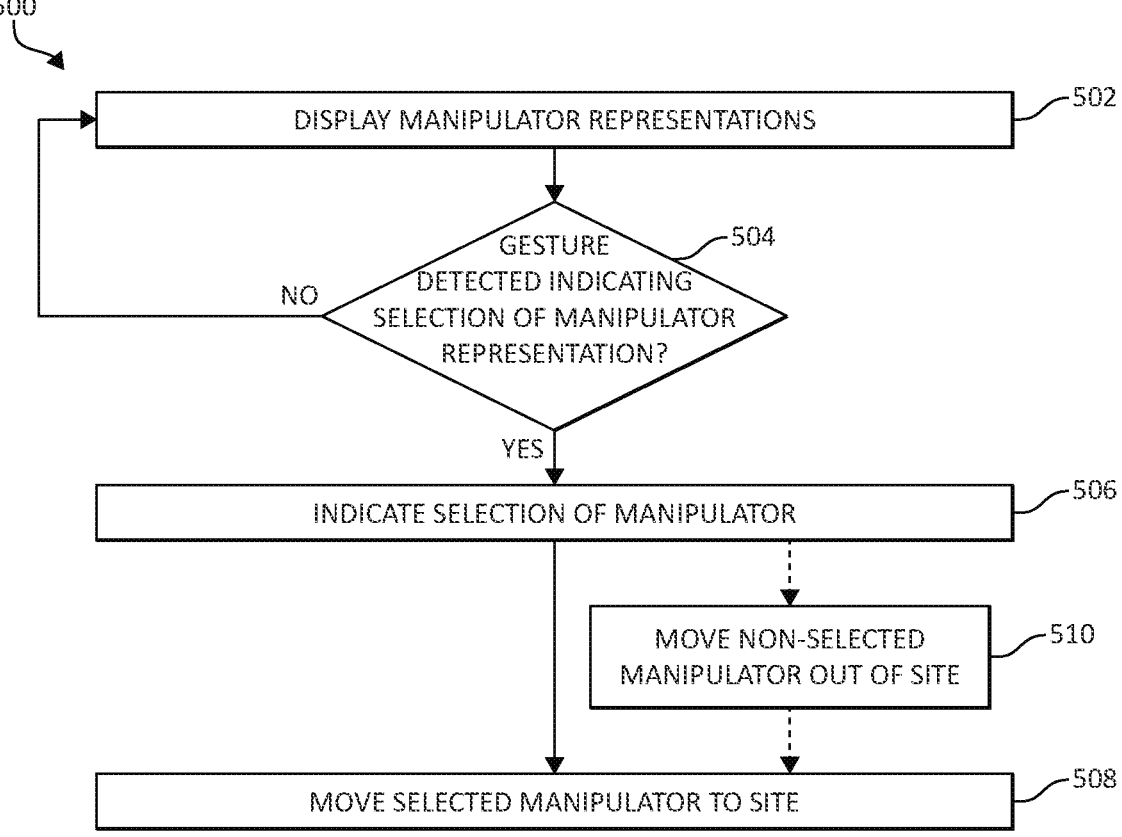
FIG. 5 is a flow diagram of a method of moving a component of the multi-input robotic surgical system based on gesture, in accordance with an embodiment.

Movement of a component based on gesture may be implemented into any one or more of the control instructions for manipulating different aspects of the manipulators and/or instruments. Turning to FIG. 5, a flow diagram of a method 500 of moving a component based on gesture, according to an embodiment, is provided. Here, movement of the component based on gesture is applied to select and move a manipulator 12 from one location to the surgical site "S". Method 500 is implemented in an embodiment in which the system 10 includes two or more manipulators 12. At step 502, the display 46 or touchscreen 50 displays representations of both manipulators 12. A determination is then made as to whether a gesture is detected indicating selection of one of the manipulator representations at step 504. If so, selection of one of the manipulators 12 corresponding to the manipulator representation is indicated at step 506, and the selected manipulator 12 is moved into the surgical site "S" at step 508. In a case in which the non-selected manipulator 12 is already at the surgical site "S", alternatively, the detected gesture may cause execution of a series of instructions that causes the non-selected manipulator 12 to move out of the surgical site "S" at step 510, and then selected manipulator 12 is moved into the surgical site "S" at step 508.

Figure 6:
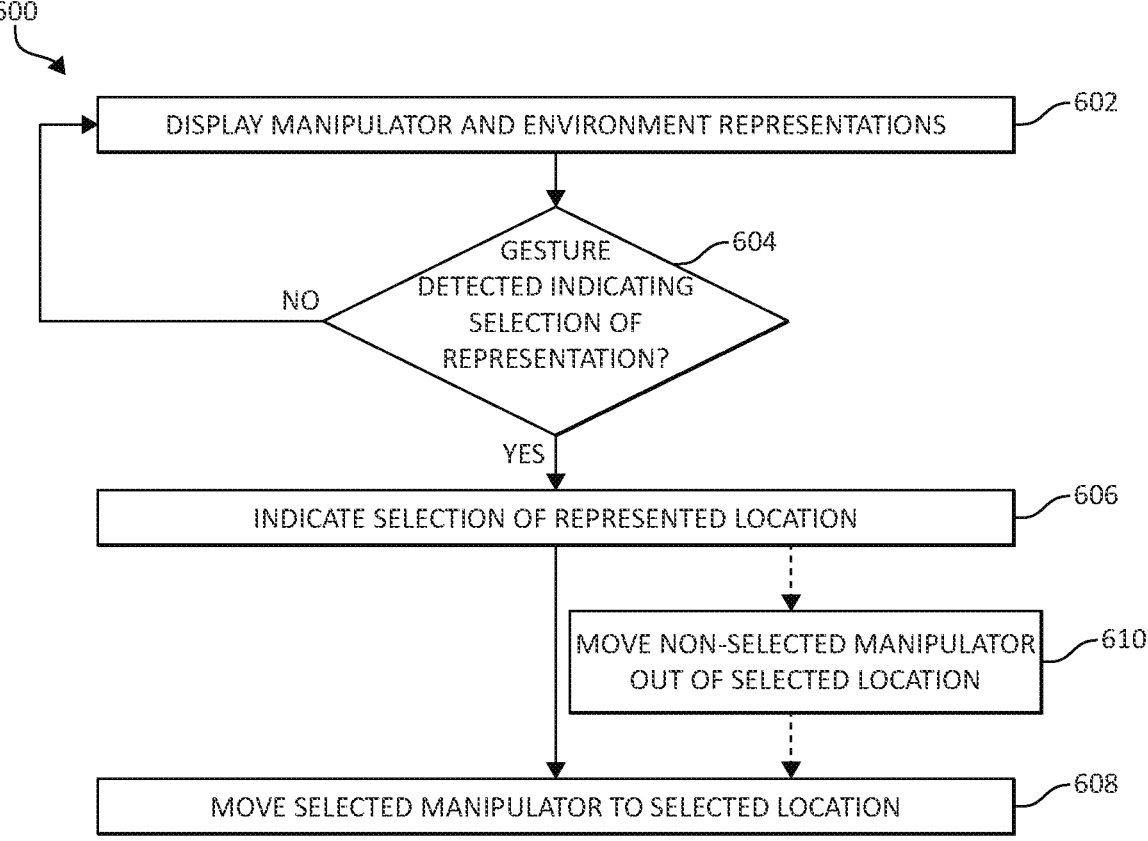
FIG. 6 is a flow diagram of a method of moving a component of the multi-input robotic surgical system based on gesture, in accordance with another embodiment.

FIG. 6 is a flow diagram of a method 500 of moving a component based on gesture, according to another embodiment. Here, movement of the component based on gesture is applied to moving a manipulator 12 from one location to another which is not the surgical site "S", according to another embodiment. The display 46 or touchscreen 50 displays a representation of a manipulator 12 in use and an environment within which the manipulator 12 is positioned, at step 602. For example, the environment includes an operating room. The display 46 or touchscreen 50 also displays various locations in the operating room represented by different representations, such as icons, numerals, letters, or other indicators. A determination is then made as to whether a gesture is detected indicating selection of one of the representations at step 604. If the selection by the detected gesture indicates one of the represented locations, the selection of the represented location is indicated at step 606, and the manipulator 12 is moved to the selected location at step 608. In case a non-selected manipulator 12 is already at the surgical site "S", alternatively, the detected gesture may cause execution of a series of instructions that causes the non-selected manipulator 12 to move out of the selected location at step 610, and then selected manipulator 12 is moved into the selected location at step 608.

Figure 7:
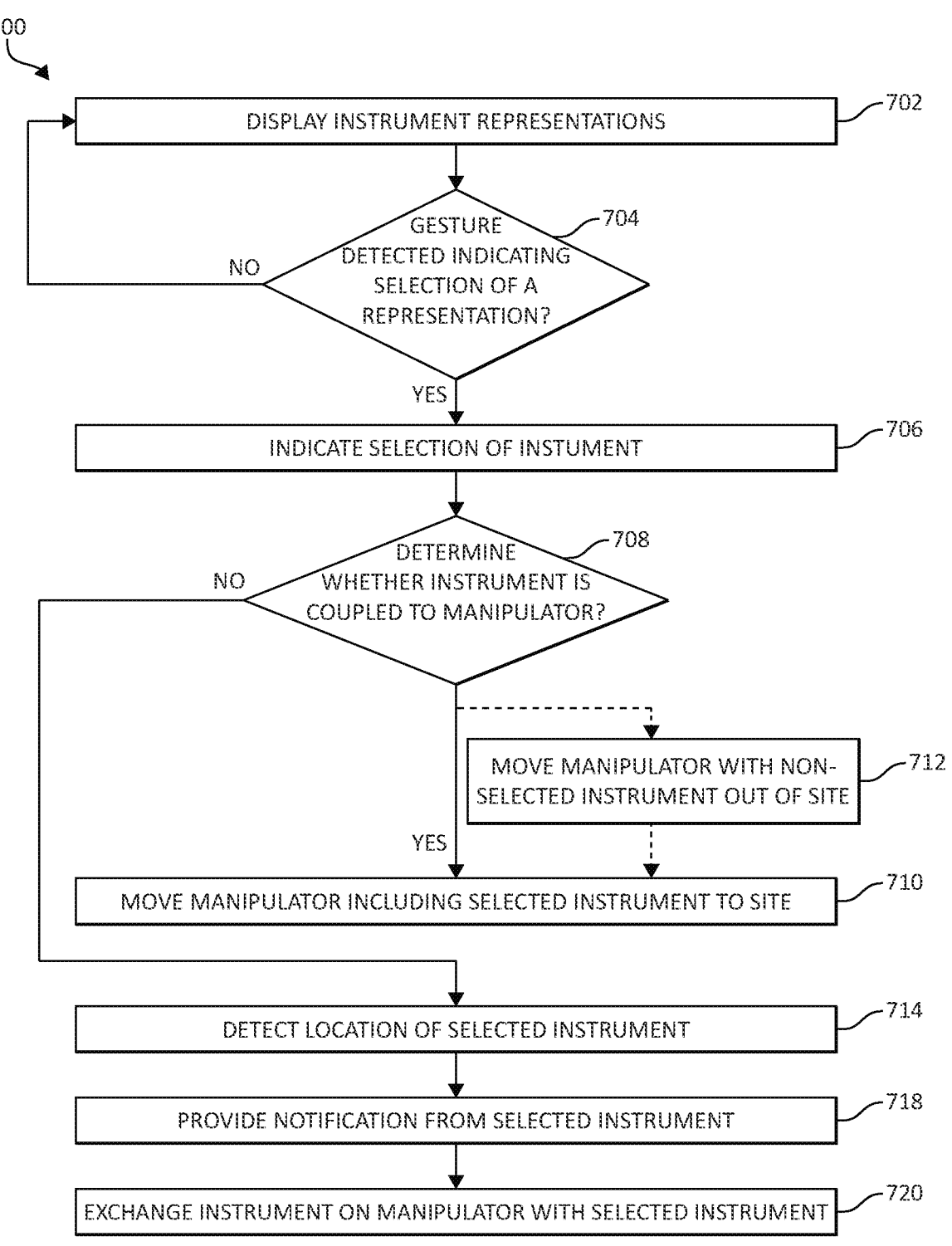
FIG. 7 is a flow diagram of a method of moving a component of the multi-input robotic surgical system based on gesture, in accordance with yet another embodiment.

In another embodiment, moving of a component based on gesture can be used for an instrument exchange involving the selection and/or coupling/decoupling of a surgical instrument 20 from a manipulator 12. FIG. 7 is a flow diagram of a method 700 of moving a component based on gesture, according to yet another embodiment. Here, at step 702, the display 46 or touch screen 50 displays a plurality of representations representing different instruments. A determination is then made as to whether a gesture is detected indicating selection of one of the representations at step 704. If the selection by the detected gesture indicates selection of a representation, a selection of one of the instruments is indicated at step 706. A determination is then made as to whether the selected instrument 20 is coupled to a robotic manipulator 12 at the surgical site "S" at step 708. If not, the robotic manipulator 12 including the selected instrument 20 moves into the surgical site "S" at step 710. In an embodiment in which the non-selected instrument 20 is already in the surgical site "S", the robotic manipulator 12 including the non-selected instrument 20 moves out of the surgical site "S" at step 712, and the robotic manipulator 12 including the selected instrument 20 move into the surgical site "S" at step 710.

Returning to step 708, if a determination is made that the selected instrument 20 is not coupled to a robotic manipulator 12 at the surgical site "S", for example, the selected instrument 20 may be located on a surgical instrument tray 70 (FIG. 1) within the operating room, a location of the selected instrument 20 is detected at step 714. The location of the instrument 20 in the operating room is tracked via radio-frequency identification tags, optical tracking of various types, such as for example shape recognition or optical codes along the lines of widely used QR codes. No matter the particular embodiment, the selected instrument 20 provides a notification at step 718, such as an audible or visible signal either emitted or displayed at a display in the operating theater, or tactile indication, which then may signal to the bedside technician to attach the selected instrument 20 to one of the manipulators 12. In another embodiment, when a gesture is detected to thereby indicate a selection of one of the instruments, a signal is sent to the manipulator 12 in use to conduct an exchange of instruments and to couple the selected instrument 20 to itself at step 720.

Figure 8:
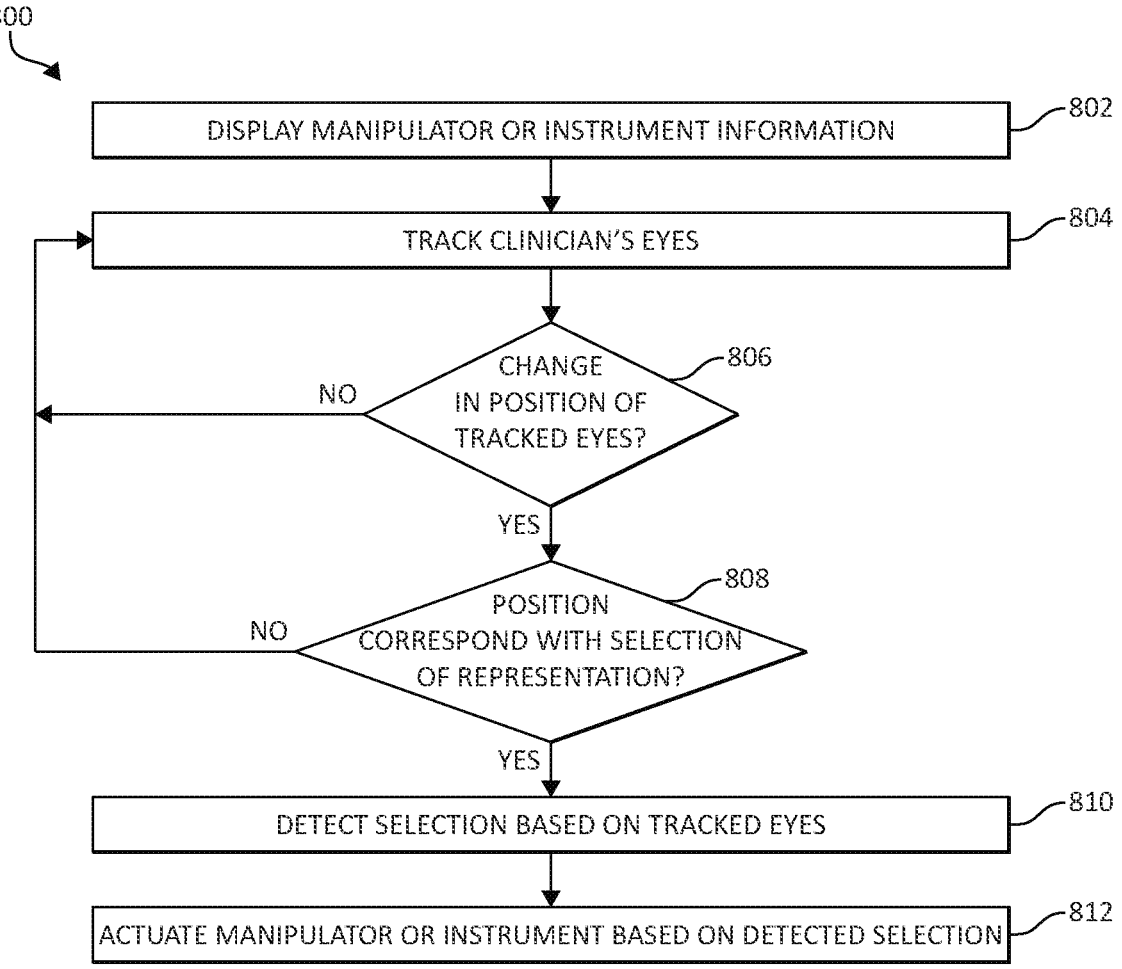
FIG. 8 is a flow diagram of a method of moving a component of the multi-input robotic surgical system based on gesture, in accordance with still another embodiment.

As discussed briefly above, rather than receiving an input using a hand gesture detected by a gesture detection sensor 48, the inputs may be detected using eye-tracking. As such, FIG. 8 is a flow diagram of an exemplary method 800 of controlling the robotic surgical system 10 using eye-tracking. In an embodiment, step 802, information relating to one or more of the robotic manipulators 12 and/or the surgical instruments 20 is displayed. For example, the information is presented as visual representations, such as pictorial icons or other graphical representation that correspond to one or more of the robotic manipulators 12 and/or instruments 20 or as text boxes indicating one or more of the robotic manipulators 12 and/or instruments 20. Additionally, the user's eyes are tracked at step 804. In an embodiment, the user image capture device 54 continuously captures images of a clinician, and the captured images are processed using known algorithms for identifying and tracking the user's eyes. In accordance with an embodiment, the captured images are processed to provide a first position of user's eyes, which indicates that the user is viewing a certain portion of the display 64. A determination is then made as to whether the user's tracked eyes have changed positions at step 806. For example, additional processing is performed to detect a change in one or more parameters associated with the tracking of the user's eyes, such as whether the change is outside of a corresponding predetermined threshold range for the parameter. If not, the method iterates at step 804. However, if a change is detected, a further determination is made as to whether the subsequent position of the user's eyes corresponds to a selection of a representation at step 806. If so, a selected representation is identified at 810 and commands are provided to actuate the manipulator or surgical instrument in a manner corresponding to the selected representation at step 812. If not, the method 800 iterates at step 804.

Each of the embodiments above may be enhanced with the implementation of voice or sound recognition. For example, prior to or concurrently with any one of the gesture detection steps (i.e., step 404 of FIG. 4, step 504 of FIG. 5, step 605 of FIG. 6, step 704 of FIG. 7) or the eye track steps (i.e., step 806 of FIG. 8), the system 10 may be configured such that the user may provide a voice command to either initiate or confirm execution of the gesture detection steps. In a similar manner, prior to or concurrently with any one of the gesture detection steps (i.e., step 404 of FIG. 4, step 504 of FIG. 5, step 605 of FIG. 6, step 704 of FIG. 7), the system 10 may be configured such that the clinician may initiate or confirm execution of the steps through eye-tracking. In such embodiment, the controller 220 may determine from images and/or video received from the image capture device 54 that the clinician is looking at his or her hands, and in response to the determination, any one of the gesture detection steps (i.e., step 404 of FIG. 4, step 504 of FIG. 5, step 605 of FIG. 6, step 704 of FIG. 7) may execute.

In still another embodiment, a gesture may be received as an input at the robotic surgical system 10, rather than at the surgeon console 40. In this regard, the gesture detected by the gesture detection sensor 56 may be translated into commands to move one or more selected robotic manipulators 12 and/or selected surgical instruments 20 in a desired manner so that the bedside assistant or a clinician in the surgical theater can move the manipulator 12 and/or surgical instrument 20 without contact.

Figure 9:
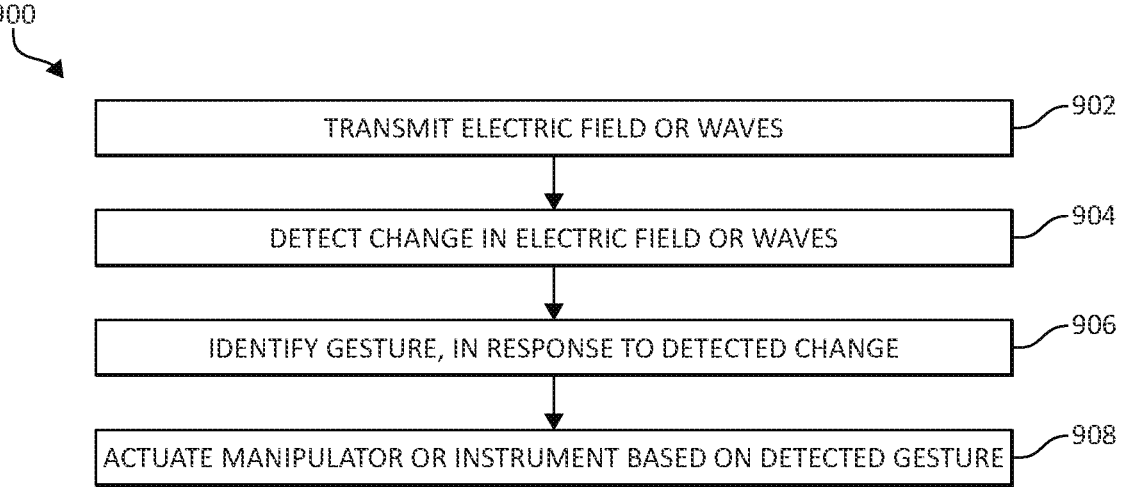
FIG. 9 is a flow diagram of a method of moving a component of the multi-input robotic surgical system based on gesture, in accordance with still yet another embodiment.

Turning now to FIG. 9, an exemplary method 900 of controlling the robotic surgical system 10 in such a manner is provided. Here, a manipulator 12 or surgical instrument 20 intended to be moved may initially be identified. For example, the gesture detection sensor 56 may be disposed directly on a manipulator 12 to be moved, and hence, the user may know at the outset which manipulator 12 is intended to be moved and selects the manipulator 12 or surgical instrument 20 by virtue of proximity. In another example, the gesture detection sensor 56 may be in the vicinity of or may be otherwise clearly associated with a manipulator 12 or surgical instrument 20, in which case, the user selects which manipulator 12 or instrument 20 in this manner. In any case, an electric field or electromagnetic waves in the radio frequency are transmitted from the gesture detection sensor 56 at step 902. For example, the gesture detection sensor 56 may be an electric field-based sensor or a radar interaction sensor, both of which are configured to generate an electric field or electromagnetic waves in the radio frequency, respectively. A change is detected in the electric field or the outputted electromagnetic waves at step 904. For example, the user's hand may enter the electric field or block or otherwise influence the outputted electromagnetic waves, for example, via a change in one or more of an amplitude or signal of the waves.

In response to the detected change, a gesture is identified at step 906. In an embodiment, a database includes data related to electric field or electromagnetic wave changes and data of corresponding gestures, and the identification is performed by matching the change to the corresponding gesture. Once the gesture is identified, the selected manipulator or surgical instrument is moved in a predetermined manner corresponding to the identified gesture at step 908. The database includes data related to a plurality of identified gestures and corresponding manners by which to actuate a manipulator or surgical instrument. For example, a gesture corresponding to a right hand swipe may correspond to a movement of the manipulator in a right-hand direction, a gesture corresponding to a left hand swipe may correspond to a movement of the manipulator in a left-hand direction, and the like.

It will further be appreciated that the embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A robotic surgical system comprising:
one or more robotic manipulators, each having a surgical instrument holder;
a surgical instrument removably coupled to the surgical instrument holder;
a user interface configured to present information related to at least one of the one or more robotic manipulators, the surgical instrument, or a surgical environment within which the surgical instrument is present, wherein the information includes a map indicating a position of the one or more robotic manipulators and surgical instruments within the surgical environment;
a gesture detection sensor configured to detect a gesture made by at least one of a hand of a user or a head of a user; and
a controller in communication with the one or more robotic manipulators, the surgical instrument, the user interface, and the gesture detection sensor and including one or more processors and one or more memories having instructions stored thereon which, when executed by the one or more processors, cause the one or more processors to:
determine whether or not a gesture indicating a selection of a first robotic manipulator of the one or more robotic manipulators has been detected;
provide one or more commands to actuate the first robotic manipulator in a predetermined manner corresponding to the detected gesture;
obtain position data including a first position and a second position of the detected gesture relative to a location on the map;
determine whether a difference between a first distance from the first position to the location and a second distance from the second position to the location is outside of a predetermined threshold range to indicate that the detected gesture corresponds to a selection of at least one of the one or more robotic manipulators or the surgical instruments; and
identify a gesture path of the detected gesture, the gesture path being within a proximity of at least one of a graphical representation of the surgical instrument or the one or more robotic manipulators on the map;
wherein, when it is determined that the gesture indicating selection of the first robotic manipulator has been detected, the one or more commands include retracting the surgical instrument holder supporting the first robotic manipulator from the surgical environment in order to decouple the surgical instrument from the first robotic manipulator and enable an instrument exchange.

2. The robotic surgical system of claim 1, wherein:
the user interface is a touch screen,
the gesture detection sensor is a touch sensor,
the presented information is a graphical representation of the surgical instrument, and
the one or more memories have stored thereon, further instructions which, when executed by the one or more processors, cause the one or more processors to determine whether or not a gesture has been detected on the touch screen over the graphical representation of the surgical instrument presented thereon, and in response to a determination that a gesture has been detected, provide the one or more commands to actuate the one or more robotic manipulators in the predetermined manner corresponding to the detected gesture.

3. The robotic surgical system of claim 1, wherein:
the user interface is a touch screen,
the gesture detection sensor is a touch sensor,
the presented information is a graphical representation of the one or more robotic manipulators, and
the one or more memories have stored thereon, further instructions which, when executed by the one or more processors, cause the one or more processors to determine whether or not a gesture has been detected on the touch screen over the graphical representation of the robotic manipulator presented thereon, and in response to a determination that a gesture has been detected, provide the one or more commands to actuate the one or more robotic manipulators in the predetermined manner corresponding to the detected gesture.

4. The robotic surgical system of claim 1, wherein:
the user interface is a display,
the gesture detection sensor is a camera sensor,
the presented information is a graphical representation of the surgical instrument, and
the one or more memories have stored thereon, further instructions which, when executed by the one or more processors, cause the one or more processors to determine whether or not a gesture has been detected by the camera sensor, and in response to a determination that a gesture has been detected, provide the one or more commands to actuate the one or more robotic manipulators in the predetermined manner corresponding to the detected gesture.

5. The robotic surgical system of claim 1, wherein:
the gesture detection sensor is an electric field-based sensor disposed on at least one of the surgical instrument or the one or more robotic manipulators, the gesture detection sensor configured to generate an electric field, and
the one or more memories have stored thereon, further instructions which, when executed by the one or more processors, cause the one or more processors to determine whether or not a gesture has been detected by the electric field-based sensor by receiving a transmission of a change in the electric field generated by the electric field-based sensor, identify a gesture based on the change in the electric field, and provide the one or more commands to actuate the one or more robotic manipulators in a predetermined manner corresponding to the identified gesture.

6. The robotic surgical system of claim 1, wherein:
the gesture detection sensor is a radar interaction sensor configured to transmit electromagnetic waves having a predetermined frequency, and
the one or more memories have stored thereon, further instructions which, when executed by the one or more processors, cause the one or more processors to determine whether or not a gesture has been detected by the radar interaction sensor by receiving a transmission of a change in one or more of an amplitude or a signal of the transmitted electromagnetic waves generated by the radar interaction sensor, identify a gesture based on the change in the one or more of an amplitude or a signal of the transmitted electromagnetic waves, and provide the one or more commands to actuate the one or more robotic manipulators in a predetermined manner corresponding to the identified gesture.

7. The robotic surgical system of claim 1, further comprising:
a user image capture device coupled to the controller and configured to capture images of the user,
wherein the one or more memories have stored thereon, further instructions which, when executed by the one or more processors, cause the one or more processors to receive the captured images of the user, track one or both of eyes of the user, identify a selection based on the tracked one or both of the eyes of the user, and provide the one or more commands to actuate the one or more robotic manipulators in a predetermined manner corresponding to the identified selection.

8. The robotic surgical system of claim 1, wherein the position data further includes a set of coordinates, velocities, location identifiers, and directional identifiers of the first position and the second position in space relative to a fixed location on the map.

* * * * *